United States Patent [19]
Bornzin et al.

[11] Patent Number: 5,810,739
[45] Date of Patent: Sep. 22, 1998

[54] METHODS AND APPARATUS FOR CLASSIFYING CARDIAC EVENTS WITH AN IMPLANTABLE CARDIAC DEVICE

[75] Inventors: Gene A. Bornzin, Simi Valley; Alan B. Vogel, Saugus; Ali Enayat Zadeh, Sierra Madre; Jonathan A. Kleks, Los Altos, all of Calif.; Raymond J. Wilson, Parker, Colo.

[73] Assignee: Pacesetter, Inc., Sylmar, Calif.

[21] Appl. No.: 770,767

[22] Filed: Dec. 19, 1996

Related U.S. Application Data

[60] Provisional application No. 60/019,064 May 9, 1996.
[51] Int. Cl.⁶ .................................................... A61N 5/0452
[52] U.S. Cl. ............................................................ 600/510
[58] Field of Search ................................... 128/696, 697, 128/699

[56] References Cited

U.S. PATENT DOCUMENTS 5,556,419  9/1996  Jarverud et al. ............................ 607/9

Primary Examiner—Scott M. Getzow

[57] ABSTRACT

Methods and apparatus are provided for classifying cardiac events with an implantable cardiac device. Cardiac signals are stored in a buffer. When a significant cardiac event is confirmed, a corresponding segment of the stored cardiac signals is processed to generate a set of feature values. The set of feature values is compared to various sets of reference values. Each set of reference values preferably corresponds to a separate type of cardiac event, so that the cardiac device may classify the significant cardiac event by matching its set of feature values to a set of reference values. Feature values include the maximum positive and negative slew rates exhibited by the cardiac signal during the segment, the maximum positive and negative signal amplitudes, the times to reach the maximum positive and negative signal amplitudes, the area under the cardiac signal curve, the area under the cardiac signal curve above zero as compared to the area below zero, and the number of zero crossings made by the cardiac signal. Additional feature values are generated by simultaneously processing the cardiac signals measured along two different vector directions in the heart.

64 Claims, 8 Drawing Sheets

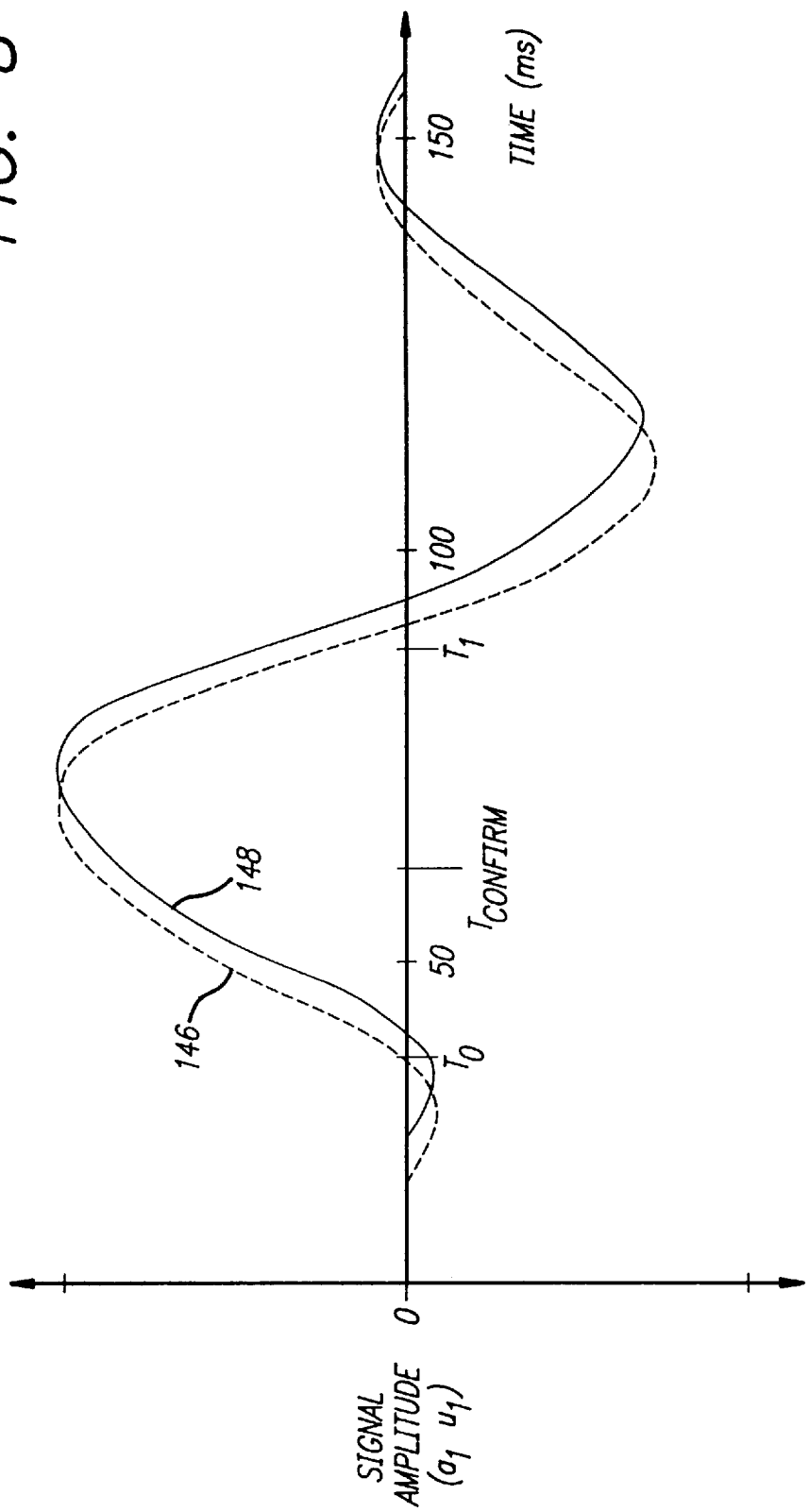

METHODS AND APPARATUS FOR CLASSIFYING CARDIAC EVENTS WITH AN IMPLANTABLE CARDIAC DEVICE

CROSS-REFERENCE

This application hereby claims priority under 35 U.S.C. §119(e) to provisional application number 60/019,064, filed May 9, 1996, which provisional application is incorporated herein in its entirety.

BACKGROUND OF THE INVENTION

This invention relates to methods and apparatus for classifying cardiac events with an implantable cardiac device.

Implantable cardiac devices, such as pacemakers, cardioverter-defibrillators, and cardiac monitoring devices, are well known. Pacemakers provide electrical pulses to a patient's heart to help maintain a healthy cardiac rhythm. Certain pacemakers, known as "demand pacemakers," provide pacing pulses only when a patient's heart fails to beat on its own. Cardioverter-defibrillators apply relatively larger pulses to terminate potentially unhealthy arrhythmias, such as an episode of tachycardia (a condition in which the heart beats too quickly) or a fibrillation event (a condition in which the heart quivers chaotically). Some sophisticated implantable cardiac devices include both pacing circuitry and cardioverter-defibrillator circuitry. Other implantable cardiac devices are only capable of monitoring a patient's heartbeat signals for diagnostic purposes.

In order to provide their various pacing, cardioversion, and defibrillation capabilities, most modern implantable cardiac devices contain sensing circuitry for monitoring the cardiac signals produced by the patient's heart. Such devices attempt to determine when and at what energy level any electrical pulses should be applied to the heart by analyzing the cardiac signals.

A typical pacemaker sensing circuit has filter and threshold detection circuitry. The filter circuitry allows signals with frequency components corresponding to cardiac events such as atrial depolarizations (P-waves) and ventricular depolarizations (R-waves) to pass to the threshold detection circuitry. The threshold detection circuitry determines whether the cardiac signals exceed a predetermined threshold. If the threshold is exceeded, the threshold detection circuitry generates an output pulse. Conventional pacemakers analyze the relative timing of the output pulses from the threshold detection circuitry to attempt to determine what type of cardiac events are occurring.

Although systems of this type are often adequate for classifying cardiac events, it would be desirable to be able to extract more detailed information from the cardiac signal. For example, there may be retrograde conduction in a patient's heart that allows pacing pulses applied to the patient's ventricle to pass to the patient's atrium. Such retrograde conduction can give rise to atrial contractions and resulting P-waves, known as "retrograde P-waves," which have amplitude and frequency characteristics similar to normal antegrade P-waves. Using conventional sensing circuitry, retrograde P-waves are often indistinguishable from antegrade P-waves.

The failure to recognize that cardiac signals in the atrium correspond to retrograde rather than antegrade P-waves can have serious consequences. If a retrograde P-wave is sensed, but is mistakenly thought to be an antegrade P-wave, a pacemaker may apply a ventricular pacing pulse in response to the sensed signal. Because such a ventricular pulse will result in another retrograde P-wave, the process may continue in an endless loop. This condition is known as pacemaker mediated tachycardia. Pacemaker mediated tachycardias are serious cardiac conditions that may lead to ventricular fibrillation. To avoid pacemaker mediated tachycardia in conventional pacemakers it is necessary to increase the post-ventricular atrial refractory period (PVARP). However, making the PVARP unduly long can lead to an undesirable condition known as 2:1 block, in which the pacemaker provides only a single ventricular pacing pulse for each two atrial beats.

Because the adverse consequences of misidentifying retrograde P-waves as normal P-waves, various techniques have been developed to attempt to accurately classify P-waves. For example, it has been observed that if the time interval between applied ventricular pacing pulses and subsequent P-waves is very regular from beat to beat, then it is likely that the P-waves are retrograde P-waves and that the patient is experiencing pacemaker mediated tachycardia. Another technique that has been developed is to vary the time at which a ventricular pacing pulse is applied and to observe if the time at which the following P-wave occurs shifts accordingly.

However, cardiac event identification techniques such as these require a precise analysis of the times at which the cardiac events are detected. These techniques may therefore be difficult to implement in practice and are slow, because the cardiac signals must be observed for a number of cardiac cycles before it is possible to determine with certainty what type of cardiac events are taking place. Further, only certain types of cardiac events can be identified in this way. If it were possible to accurately identify more cardiac events, it would be possible to improve the operation of implantable cardiac devices under a variety of conditions.

Implantable cardiac devices are connected to a patient's heart by leads. A single lead may be used for pacing and sensing in a single heart chamber or two leads may be used for atrial and ventricular pacing and sensing. Both unipolar and bipolar leads are commonly used. Unipolar leads contain a single electrode. In applying a pulse to the heart using a unipolar lead, the pulse voltage is applied between the unipolar lead electrode and the metal case of the pacemaker. Cardiac signals are sensed across the unipolar lead electrode and the case. Bipolar leads contain two electrodes: a tip electrode and a ring electrode. Pacing and sensing with bipolar leads typically takes place across the tip and ring electrodes.

Unipolar leads are typically more susceptible to electromyographic interference (noise from the depolarization of skeletal muscles) than bipolar leads. Electromyographic interference is of particular concern when sensing signals in the atrium, because atrial signals are smaller than ventricular signals. Pacemakers have therefore been developed that are configured to sense atrial signals by measuring the signal between an atrial unipolar lead electrode and a ventricular unipolar lead electrode. Ventricular sensing in this type of pacemaker occurs between the ventricular electrode and the pacemaker case. Atrial pacing pulses are provided across the atrial electrode and the pacemaker case. Ventricular pacing is done between the ventricular electrode and the case. Although such electrode configurations are generally less susceptible to electromyographic interference than other configurations, the electrode configuration is fixed. It is therefore not possible to measure cardiac signals using other electrode arrangements, even if such arrangements would provide useful information for classifying various cardiac events.

Thus, what is needed is an improved method and apparatus for classifying cardiac signals with an implantable cardiac stimulating device.

What is also needed is a method and apparatus for classifying cardiac events by simultaneously processing the cardiac signals measured along two different vector directions in the heart and comparing these signals.

SUMMARY OF THE INVENTION

In accordance with the principles of the present invention, methods and apparatus are provided for classifying cardiac events with an implantable cardiac device. The cardiac device senses cardiac signals received via various lead electrodes and stores the signals in a buffer, which is preferably formed from a portion of a memory device. The cardiac device preferably contains a control unit that executes instructions stored in the memory. The control unit and sensing circuitry within the cardiac device are used to detect significant cardiac events.

When a significant cardiac event is confirmed, the cardiac device processes a corresponding segment of the stored cardiac signals to generate a set of representative feature values. The set of feature values is compared to a number of predetermined sets of reference values using any suitable technique. If desired, the feature values can be compared to the reference values by calculating the sum of the absolute values of the differences between each feature value and a corresponding reference value. The implantable cardiac device identifies the set of reference values that most closely matches the measured feature value set based on the comparison of the feature values to the reference values. Because each set of reference values preferably corresponds to a separate type of cardiac event, matching the set of feature values to a set of reference values allows the cardiac device to classify the measured cardiac event.

Feature values that may be calculated include the maximum positive and negative slew rates exhibited by the cardiac signal, the maximum positive and negative signal amplitudes, the times to reach the maximum positive and negative signal amplitudes, the area under the cardiac signal curve, the area under the cardiac signal curve above zero as compared to the area below zero, and the number of zero crossing made by the cardiac signal. Additional feature values are generated by simultaneously processing the cardiac signals measured along two different vector directions in the heart. The signals for each vector are measured using separate channels of sensing circuitry.

If desired, the sensing circuitry for each channel can include filters, an amplifier, a threshold detector, and an analog-to-digital converter. Multiplexing circuitry is preferably used to connect a suitable set of electrodes to the sensing circuitry. Electrodes can be selected from among the atrial tip, atrial ring, ventricular tip, ventricular ring, and case electrodes.

The process of generating additional feature values by simultaneously processing the cardiac signal measured along two different vector directions in the heart may involve extracting information based on a graphical representations of the vector information. For example, a curve may be formed by plotting the cardiac signals received from two vectors along two orthogonal axes of a graph. One feature vector that can be extracted from this type of representation is the quadrant in which the curve originates when a significant cardiac event is detected. Another feature vector that can be extracted is the quadrant in which the curve ends at the termination of the significant cardiac event. Further, whether the curve has a clockwise or a counter-clockwise rotation is an additional feature that can be obtained from the cardiac signal segment. Feature values based on the trajectories of the curve can also be calculated at various points.

BRIEF DESCRIPTION OF THE DRAWINGS

The above and other advantages of the invention will be apparent upon consideration of the following detailed description, taken in conjunction with the accompanying drawings, in which like reference numerals refer to like parts throughout, and in which:

FIG. 8 is an idealized retrograde P-wave (the solid line represents the signal detected between the atrial ring electrode and the case electrode and the dashed line represents the signal detected between ventricular ring electrode and the case electrode)

DETAILED DESCRIPTION OF THE PREFERRED EMBODIMENTS

Figure 1:
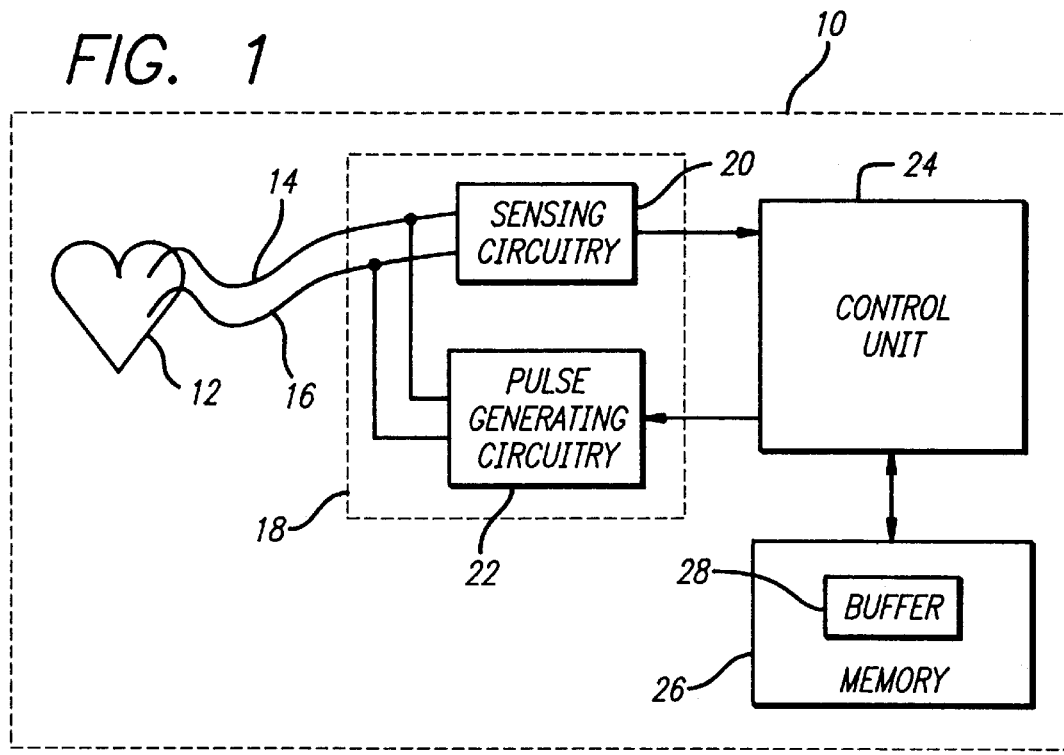
FIG. 1 is a schematic block diagram of an implantable cardiac device in accordance with the present invention.

An implantable cardiac device 10, which is connected to a patient's heart 12 via leads 14 and 16, is shown in FIG. 1. The implantable cardiac device 10 has interface circuitry 18 for connecting the leads 14 and 16 to a control unit 24. The control unit 24 preferably contains dedicated control and processing circuitry and is microprocessor-based. The interface circuitry 18 preferably contains sensing circuitry 20 for sensing cardiac signals across the leads 14 and 16 and pulse generating circuitry 22 for providing output pulses to the heart 12 via the leads 14 and 16. If the implantable cardiac device 10 is used solely to provide cardiac monitoring functions, the pulse generating circuitry 22 is not needed.

The control unit 24 is connected to a memory 26, which preferably contains a buffer 28 for storing cardiac signals. The memory 26 stores instructions that are executed by the control unit 24 during the operation of the implantable cardiac device 10.

The leads 14 and 16 are used to apply electrical pulses to the heart and to sense cardiac signals. A variety of lead arrangements are available. One commonly used lead is the bipolar lead. If a first bipolar lead is implanted in the right atrium of a patient's heart and a second bipolar lead is implanted in the right ventricle, a dual chamber cardiac device can sense and apply pulses in both the atrium and the ventricle. If desired, unipolar leads may be used.

Figure 2:
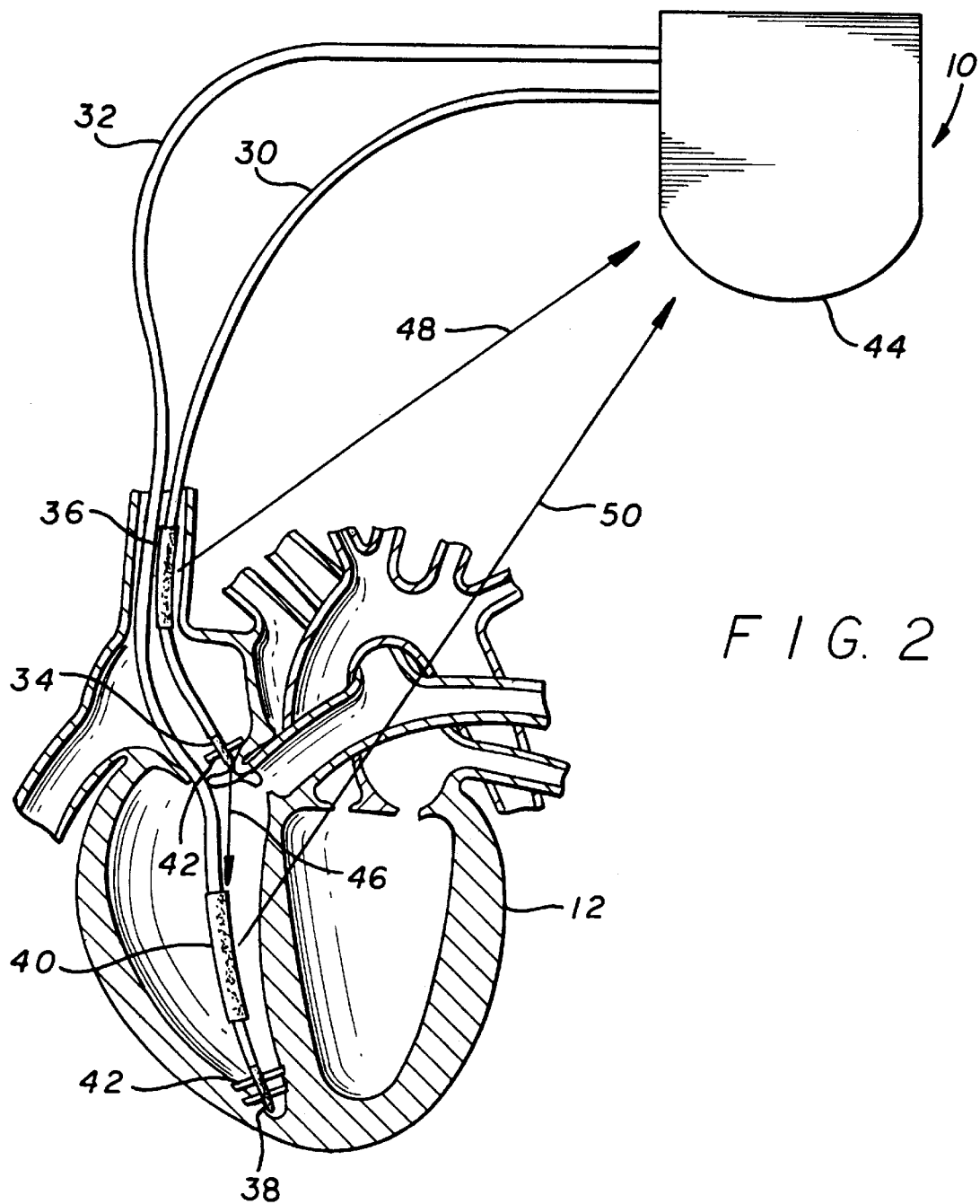
FIG. 2 is a view of the implantable cardiac device of the present invention showing two illustrative vectors.

If the leads 14 and 16 (FIG. 1) are of the bipolar type, the implantable cardiac device 10 is preferably coupled to the heart 12 via atrial bipolar lead 30 and ventricular bipolar lead 32, as shown in FIG. 2. The bipolar lead 30 has an atrial tip electrode 34 ($A_{TIP}$) and an atrial ring electrode 36 ($A_{RING}$). The bipolar lead 32 has a ventricular tip electrode 38 ($V_{TIP}$) and a ventricular ring electrode 40 ($V_{RING}$). The tip electrodes 34 and 38 are typically attached to the heart wall using tines 42 although other fastening mechanisms may be used, such as screws. The implantable cardiac device 10 is housed in a metal case 44 (CASE).

In a conventional dual chamber pacemaker with bipolar leads, one bipolar lead is used for sensing and pacing in the atrium (using the $A_{TIP}$ and $A_{RING}$ electrodes) and one bipolar lead is used for sensing and pacing in the ventricle (using the $V_{TIP}$ and $V_{RING}$ electrodes). Conventional dual chamber unipolar pacemakers, which have no RING electrodes, sense and pace between $A_{TIP}$ and CASE for the atrium and between $V_{TIP}$ and CASE for the ventricle. In another conventional unipolar arrangement, atrial sensing is performed using the electrode pair $A_{TIP}$ and $V_{TIP}$; atrial pacing is performed using the electrode $A_{TIP}$ and CASE; ventricular sensing and pacing is performed using $V_{TIP}$ and CASE. None of these conventional lead configurations can be changed during the operation of the pacemaker. Further, only limited information, such as the time at which a cardiac event occurs, can be derived using conventional arrangements.

With the present invention, the sensing circuitry 20 (FIG. 1) and the pulse generating circuitry 22 (FIG. 1) can be selectively interconnected with different electrodes ($A_{TIP}$, $A_{RING}$, $V_{TIP}$, $V_{RING}$, and CASE) during operation, as desired. When certain electrode pairs are selected, the sensing circuitry 20 (FIG. 1) is capable of monitoring the cardiac signals that occur along different vectors through the cardiac tissue. For example, as shown in FIG. 2, when sensing is performed using the atrial tip electrode 34 and the ventricular ring electrode 40, signals are measured along a vector 46. When sensing is performed using the atrial ring electrode 36 and the case 44, signals are measured along a vector 48. Sensing between the ventricular ring electrode 40 and the case 44 measures signals along vector 50.

The specific electrode pairs that are used for sensing can be selected by a physician to suit the needs of an individual patient or can be selected by the implantable cardiac device 10 itself, based on instructions previously stored in the memory 26 (FIG. 1). Further, signals from more than one pair of electrodes may be monitored at the same time, which allows the implantable cardiac device 10 to simultaneously process and compare the cardiac signals along two different vectors. Monitoring cardiac signals using two electrode pairs at once so that the signal measured along one vector can be compared with the signal measured along the other allows the implantable cardiac device 10 to classify cardiac events much more accurately than if only a single pair of electrodes were used.

The implantable cardiac device 10 classifies cardiac events more accurately than conventional cardiac devices because whenever a cardiac event is detected the implantable cardiac device 10 analyzes the segment of the cardiac signal representing the cardiac event to determine its unique features. The implantable cardiac device 10 generates a set of feature values for each segment of the cardiac signal that is analyzed. The set of feature values for the cardiac signal segment is compared to various predetermined sets of reference values, each of which corresponds to a particular known type of cardiac event. If the set of measured feature values closely matches one of the sets of predetermined reference values, then the cardiac event is classified as corresponding to cardiac events of the type associated with that set of reference values.

Figure 3A:
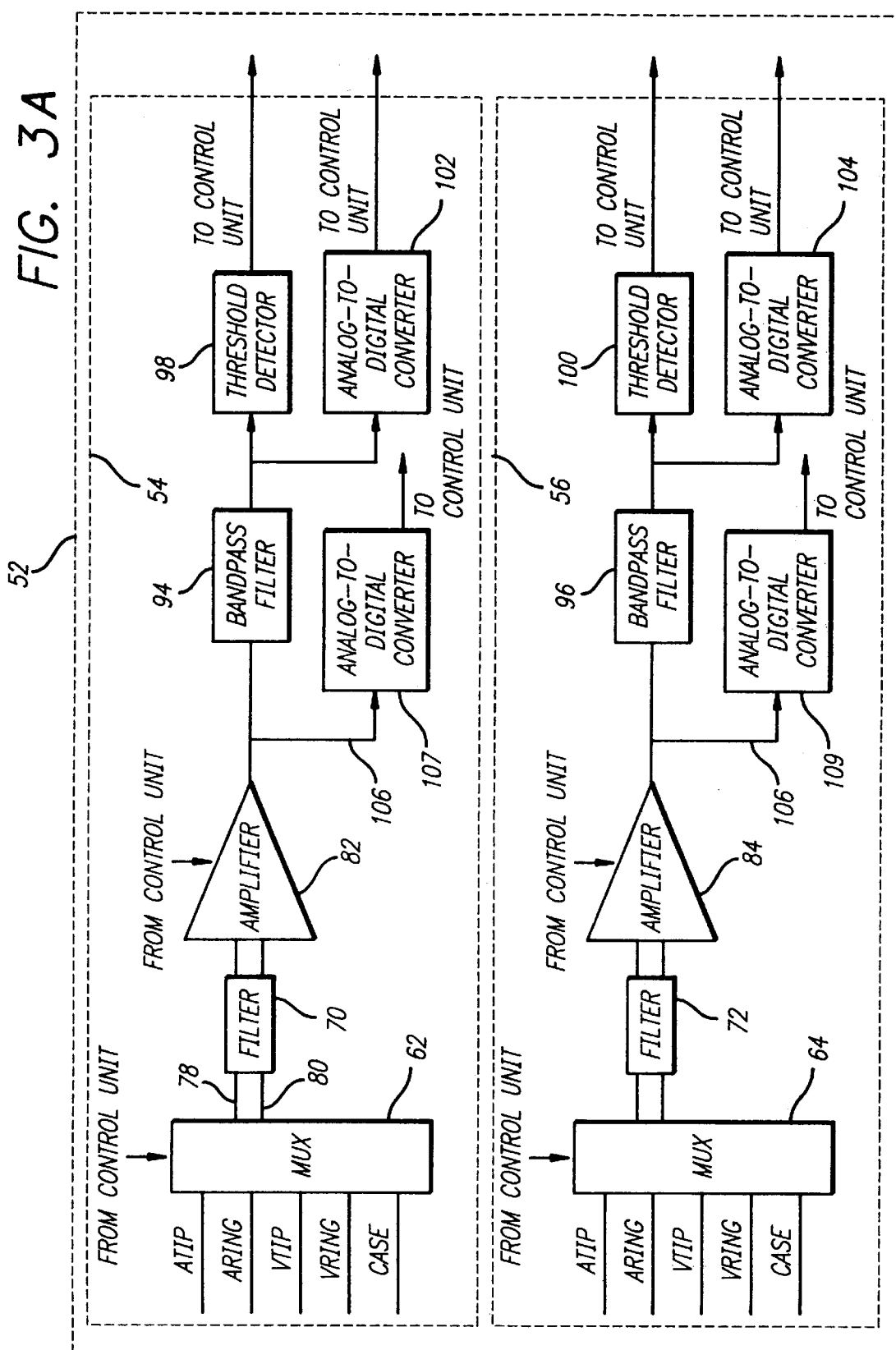
FIGS. 3A and 3B show a schematic block diagram of illustrative sensing circuitry for the implantable cardiac device of the present invention.
Figure 3B:
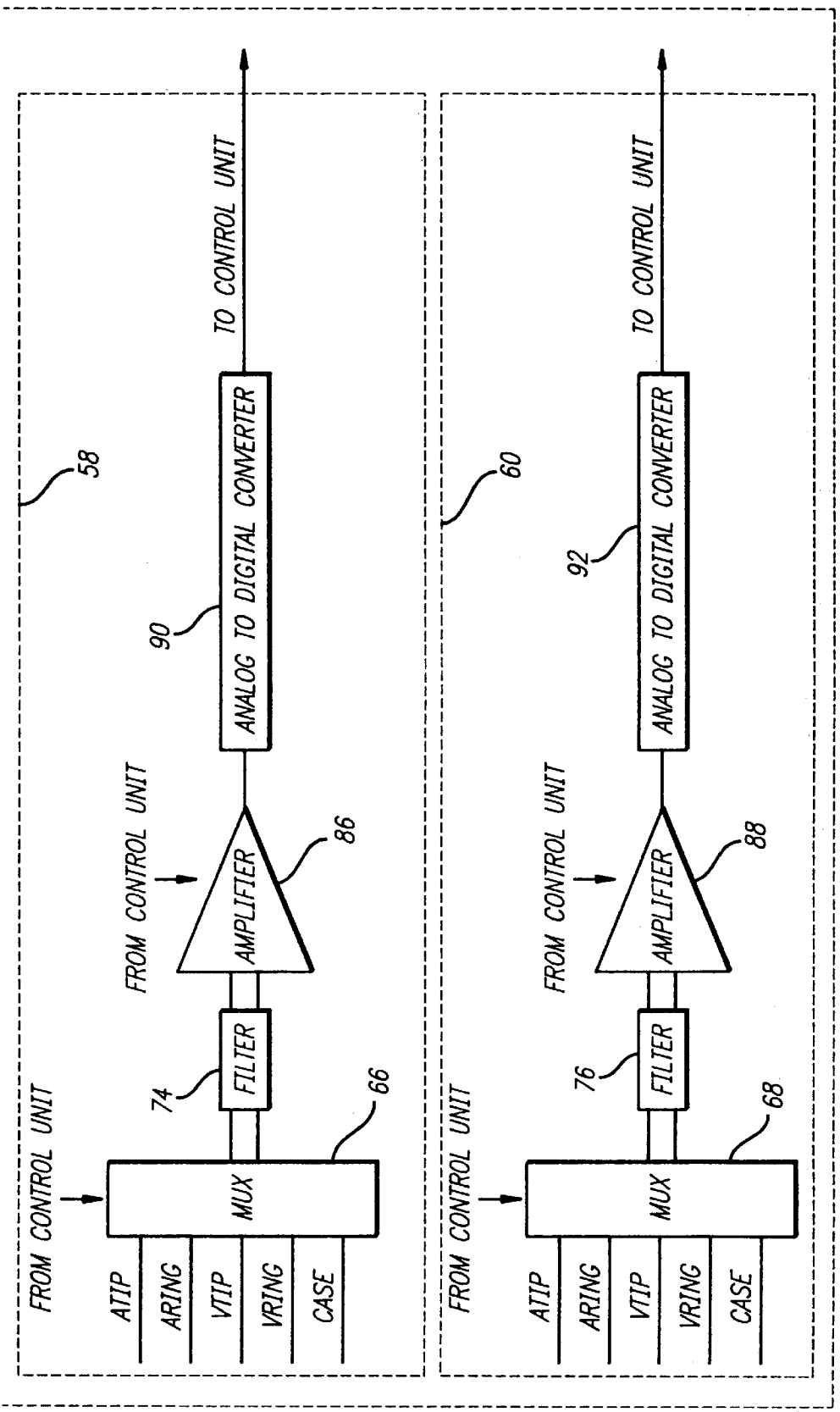

Suitable sensing circuitry 52 for processing signals from the leads 14 and 16 (FIG. 1) is shown in FIGS. 3A and 3B. The sensing circuitry 52 has atrial sensing circuitry 54, ventricular sensing circuitry 56, atrial intracardiac electrogram circuitry 58, and ventricular intracardiac electrogram circuitry 60. Multiplexers 62, 64, 66, and 68 receive signals from the electrodes $A_{TIP}$, $A_{RING}$, $V_{TIP}$, $V_{RING}$, and CASE and distribute the signals across desired pairs of electrodes to filters 70, 72, 74, and 76, respectively. For example, the multiplexer 62 can connect the $A_{RING}$ and CASE electrodes to input lines 78 and 80 of the filter 70, respectively. If desired, each of the multiplexers 62, 64, 66, and 68 may couple a different pair of electrodes to its respective filter. The filters 70, 72, 74, and 76 preferably filter out signals with frequencies less than 1 Hz (typically associated with noise) and frequencies greater than one-half of the rate at which the cardiac signal is sampled (typically about 1 kHz).

Each of the atrial sensing circuitry 54, the ventricular sensing circuitry 56, the atrial intracardiac electrogram circuitry 58, and the ventricular intracardiac electrogram circuitry 60 preferably is connected to a respective one of amplifiers 82, 84, 86, and 88, which increase the signal strength of the measured cardiac signals. Preferably, the multiplexers 62, 64, 66, and 68 and the amplifiers 82, 84, 86, and 88 receive control signals from the control unit 24 (FIG. 1). The control signals specify which of the electrodes the multiplexers 62, 64, 66, and 68 are to couple to filters 70, 72, 74, and 76. The control signals also specify the programmable gain for the amplifiers 82, 84, 86, and 88.

Atrial intracardiac electrogram circuitry 58 contains an analog-to-digital converter 90 to digitize the output of the amplifier 86. The analog-to-digital converter 90 provides the digitized output of the amplifier 86 to the control unit 24 (FIG. 1). The atrial intracardiac electrogram circuitry 58 is generally used to measure atrial cardiac signals. Accordingly, the multiplexer 66 typically connects the filter 74 across an electrode pair such as $A_{TIP}$ and $A_{RING}$, $A_{TIP}$ and CASE, or $A_{RING}$ and CASE.

Ventricular intracardiac electrogram circuitry 60 contains an analog-to-digital converter 92 to digitize the output of the amplifier 88. The digitized output from the analog-to-digital converter 92 is provided to the control unit 24 (FIG. 1). The ventricular intracardiac electrogram circuitry 60 is generally used to measure ventricular cardiac signals. Accordingly, the multiplexer 68 connects the filter 76 across an electrode pair such as $V_{TIP}$ and $V_{RING}$, $V_{TIP}$ and CASE, or $V_{RING}$ and CASE.

The digitized signals from the analog-to-digital converters 90 and 92 are provided to control unit 24 (FIG. 1). These signals are preferably stored in the buffer 28 (FIG. 1). The control unit 24 (FIG. 1) can analyze the signals stored in buffer 28 (FIG. 1) to classify the type of cardiac event that has been sensed. If desired, the signals in buffer 28 can also be transmitted using conventional telemetry techniques, so that an external receiver (not shown) may display and analyze the signals.

The atrial sensing circuitry 54 processes the signals from the pair of electrodes selected by multiplexer 62 that are suitable for measuring an atrial signal (typically a pair of electrodes such as $A_{TIP}$ and $A_{RING}$, $A_{TIP}$ and CASE, or $A_{RING}$ and CASE). The ventricular sensing circuitry 56 processes the signals from the pair of electrodes selected by multiplexer 64 that are suitable for measuring a ventricular signal (typically a pair of electrodes such as $V_{TIP}$ and $V_{RING}$, $V_{TIP}$ and CASE, or $V_{RING}$ and CASE). The atrial sensing circuitry 54 preferably has a bandpass filter 94 and the ventricular sensing circuitry 56 preferably has a bandpass filter 96. The bandpass filters 94 and 96 are preferably two cascaded second-order bandpass filters with Q=0.365, a passband of approximately 23–110 Hz, and a center frequency of 50 Hz.

The bandpass filters 94 and 96 filter out the components of the cardiac signals received from amplifiers 94 and 96 that do not correspond to cardiac events such as P-waves or R-waves. The output of the bandpass filter 94 is provided to a threshold detector 98. When a signal entering the threshold detector 98 exceeds a predetermined threshold, the threshold detector 98 generates a corresponding output pulse, which is provided to the control unit 24 (FIG. 1). The output pulse from the threshold detector 98 indicates that the atrial sensing circuitry 54 has detected the occurrence of a cardiac event such as a P-wave.

The ventricular sensing circuitry 56 has a threshold detector 100 that operates similarly to the threshold detector 98. The output of the bandpass filter 96 is provided to the threshold detector 100, which generates an output pulse when the signal exceeds a predetermined threshold. When the threshold detector 100 generates an output pulse, it indicates that the ventricular sensing circuitry 56 has detected the occurrence of a cardiac event such as an R-wave.

If desired, the implantable cardiac device 10 can be controlled by the control unit 24 (FIG. 1) based on the relative timing of the output pulses received from the threshold detectors 98 and 100. This basic mode of operation is similar to that of a conventional pacemaker. However, the operation of conventional pacemakers is based solely on monitoring the relative timing of the occurrences of cardiac events as detected by the pacemaker's atrial and ventricular channels of sensing circuitry. With the present invention, the control unit 24 (FIG. 1) classifies cardiac events by processing the cardiac signal received from the analog-to-digital converters 90, 92, 102, and 104, as well as the output signals from the threshold detectors 98 and 100. Further, with the multiplexers 62, 64, 66, and 68, the sensing circuitry 52 can select and simultaneously process signals from more than one pair of the $A_{TIP}$, $A_{RING}$, $V_{TIP}$, $V_{RING}$, or CASE electrodes, which allows cardiac signals along more than one vector (such as the vectors 48 and 50 of FIG. 2) to be analyzed at one time. Comparing the cardiac signals measured along two distinct vectors provides information that distinguishes cardiac events from one another that would otherwise be difficult or impossible to accurately classify.

The sensing circuitry 52 is preferably capable of selecting electrode pairs and filtering, amplifying, and digitizing the signals from the electrode pairs as needed to provide sufficient data to the control unit 24 (FIG. 1) for implementing the various classification schemes described below. It is not necessary that the sensing circuitry 52 have the precise configuration shown in FIGS. 3A and 3B. For example, the multiplexers 62, 64, 66, and 68 could be combined into a single multiplexer with multiple outputs. The analog-to-digital converters 90, 92, 102 and 104 could be combined into one multiple-channel analog-to-digital converter, or a single-channel analog-to-digital converter could be used if provided with a suitable multiplexed input.

Further, the way in which the circuit components shown in the sensing circuitry 52 are interconnected may be altered. If desired, the multiplexers 62, 64, 66, and 68 could be provided after the filtering and amplifying functions of the filters 70, 72, 74, 76 and amplifiers 82, 84, 86, and 88 are performed. The filtering properties of filters 70, 72, 74, and 76 and the amplifying properties of amplifiers 82, 84, 86, and 88 could also be provided by circuitry that is integrated elsewhere within the sensing circuitry 52. Using four channels of circuitry rather than two channels allows cardiac signals across a greater number of combinations of electrode pairs to be digitized for processing by the control unit 24. However, using four channels of circuitry is more complex than using two channels of circuitry. Therefore, although the sensing circuitry 52 is shown with four channels of sensing and processing circuitry (the atrial sensing circuitry 54, the ventricular sensing circuitry 56, the atrial intracardiac electrogram circuitry 58, and the ventricular intracardiac electrogram circuitry 60), if desired, only two channels of circuitry need be used. For example, the intracardiac electrogram signals that are digitized by the analog-to-digital converters 90 and 92 could be provided to analog-to-digital converters 107 and 109 connected to output terminals 106 and 108 of the atrial sensing circuitry 54 and the ventricular sensing circuitry 56, respectively.

As shown in FIG. 1, during operation of the implantable cardiac device 10 cardiac signals from the electrodes ($A_{TIP}$, $A_{RING}$, $V_{TIP}$, $V_{RING}$, and CASE) are provided to the control unit 24, which stores digitized data corresponding to these signals in the buffer 28. Preferably, the buffer 28 is formed from a region of the memory 26, although, if desired, the buffer 28 can be provided as a separate storage device. The buffer 28 is preferably large enough for storing a segment of each of the signals received and digitized by the analog-to-digital converters 90, 92, 102, and 104 or the analog-to-digital converters 107 and 109 connected to output terminals 106 and 108. If desired, the buffer 28 may be organized in the form of a circular buffer, in which the most recently received data are stored in place of the oldest data in the buffer. Preferably, data from each of the analog-to-digital converters 90, 92, 102, and 104 are stored, although if it is desired to conserve memory, only data from analog-to-digital converters 90 and 92 are stored. The step of using the control unit 24 (FIG. 1) to store the digital cardiac signals from the atrial sensing circuitry 54, the ventricular sensing circuitry 56, the atrial intracardiac electrogram circuitry 58, and the ventricular intracardiac electrogram circuitry 60 is shown as step 110 of FIG. 4.

The step 110 of storing cardiac signals in the buffer 28 (FIG. 1) is preferably an ongoing one, so that the most recent cardiac data are always present in the buffer 28 (FIG. 1). At step 112, the implantable cardiac device 10 (FIG. 1) confirms that a significant cardiac event has occurred. One suitable way in which significant cardiac events may be confirmed is by using the atrial sensing circuitry 54 (FIG. 3A) and the ventricular sensing circuitry 56 (FIG. 3A). When cardiac signals that have been filtered and amplified by the atrial sensing circuitry 54 (FIG. 3A) and the ventricular sensing circuitry 56 (FIG. 3A) exceed predetermined threshold values, the threshold detectors 98 and 100 (FIG. 3A) generate corresponding output pulses that indicate the occurrence of significant cardiac events.

Whenever the presence of a significant cardiac event has been confirmed, the control unit 24 (FIG. 1) processes a suitable corresponding segment of the cardiac data stored in the buffer 28 (FIG. 1) to attempt to classify the event. The segment may be from one or more channels of the sensing circuitry 52 (FIGS. 3A and 3B). For example, the segment may consist of a portion of the cardiac signal from the output of the analog-to-digital converter 90 (FIG. 3A) and a portion of the cardiac signal from the output of the analog-to-digital converter 92 (FIG. 3B).

If desired, the segment that is processed may represent a subset of the cardiac data that are stored in the buffer 28 (FIG. 1). Alternatively, the segment can include all of the cardiac data stored in the buffer 28 (FIG. 1). Cardiac data that are measured immediately following the confirmation of the significant cardiac event can also be included in the segment by waiting until the digital representations of these data signals have been stored in the buffer 28 (FIG. 1) before retrieving the data segment for processing. The segment of cardiac data is preferably long enough (approximately 50–100 ms) to cover the duration of a typical cardiac event such as a P-wave or an R-wave. The precise length and position of the segment that is used may be selected by the physician or may be based on predetermined criteria.

The segments of cardiac data are characterized by numerous features, such as maximum slew rate or amplitude, that are used to accurately classify cardiac events. Additional features can be generated by simultaneously analyzing and comparing the cardiac signals measured along two different vectors within the body (such as the vectors 48 and 50 of FIG. 2).

Figure 4:
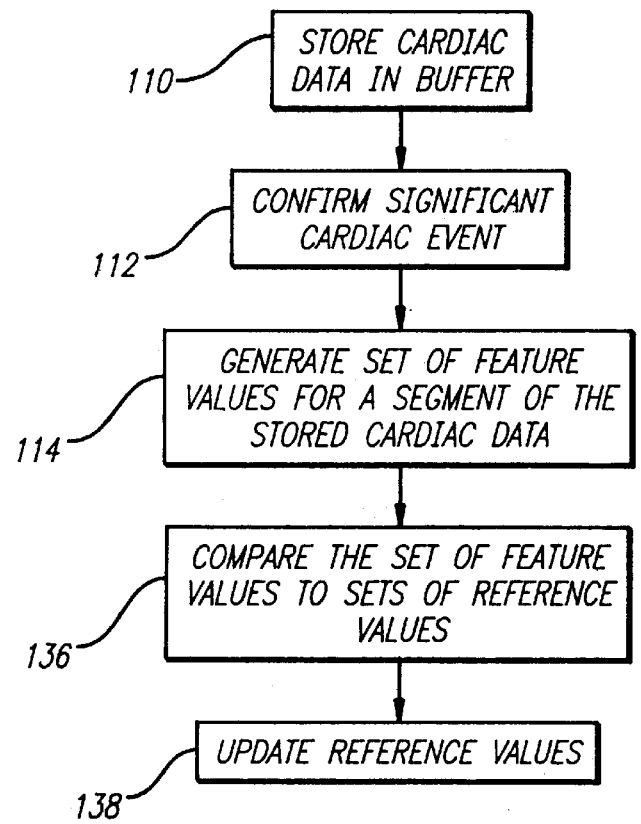
FIG. 4 is a flow chart showing the steps involved in classifying a cardiac event in accordance with the present invention.
Figure 5:
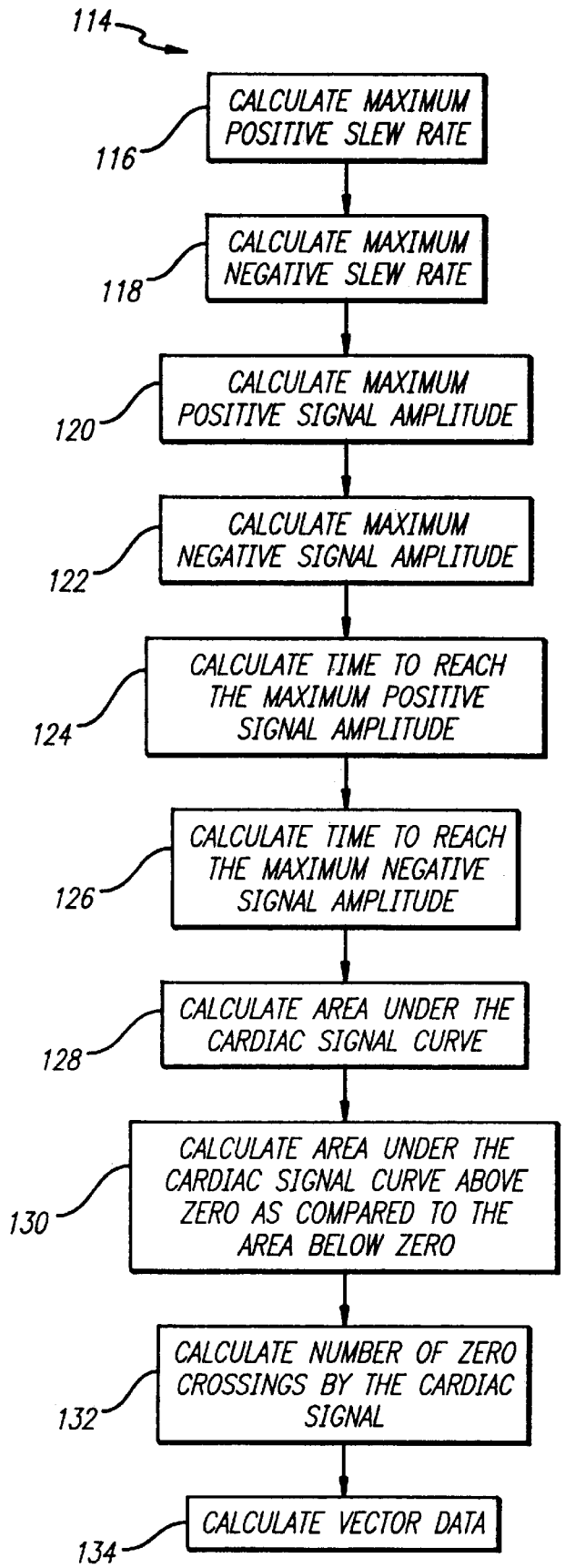
FIG. 5 is a flow chart showing the steps involved in generating a set of feature values corresponding to a given segment of a cardiac signal.

As shown in FIG. 4, after a significant cardiac event is confirmed at the step 112, the control unit 24 (FIG. 1) processes the segment of stored cardiac data to generate a set of feature values at step 114. Each set is preferably made up of at least three feature values. As shown in greater detail in FIG. 5, the step 114 of generating the set of feature values may include a step 116 of calculating the maximum positive slew rate exhibited by the cardiac signal during the segment and a step 118 of calculating the maximum negative slew rate. If desired, the maximum slew rate (whether positive or negative) may be calculated.

The step 114 of generating a set of feature values may also include a step 120 of calculating the maximum positive signal amplitude and a step 122 of calculating the maximum negative signal amplitude. A maximum amplitude (positive or negative) may also be calculated. Additional steps include a step 124 of calculating the time to reach the maximum positive signal amplitude, a step 126 of calculating the time to reach the maximum negative signal amplitude, a step 128 of calculating the area under the cardiac signal curve, a step 130 of calculating the area under the cardiac signal curve above zero as compared to the area below zero, and a step 132 of calculating the number of zero crossing made by the cardiac signal. The step 130 may involve calculating the ratio of the area under the cardiac signal curve above zero to the area below zero or may involve calculating the difference between the area under the cardiac signal curve above zero and the area below zero.

The step 114 of generating a set of feature values also preferably includes a step 134 of calculating vector data. The step 134 involves simultaneously processing and comparing the cardiac signals measured along two different vectors (such as the vectors 48 and 50 of FIG. 2). The signals for each vector are measured using separate channels of sensing circuitry (such as the atrial intracardiac electrogram circuitry 58 (FIG. 3B) and the ventricular intracardiac electrogram circuitry 60 (FIG. 3B)). The simultaneous processing and comparing of signals measured along two vectors during the step 134 allows additional feature values to be generated, which can be used to classify cardiac events. For example, if the cardiac signals measured along a first vector are particularly sensitive to signals originating in the atria, whereas cardiac signals measured along a second vector are particularly sensitive to cardiac signals originating in the ventricles, then simultaneously processing and comparing the signals from both of these vectors yields feature values that can indicate whether the patient is experiencing normal or retrograde P-waves.

Preferably, each significant type of cardiac event can be classified by a unique set of features. For example, typical normal P-waves have known maximum positive and negative slew rates, maximum positive and negative amplitudes, and various other attributes that set P-waves apart from other cardiac events. The unique set of feature values for a given cardiac event is called a set of "reference values." Reference values can be determined empirically, either by analyzing the cardiac signals of an individual patient or by statistically analyzing the cardiac signals of a group of patients. A set of reference values is preferably generated for each known type of cardiac event. Examples of typical types of cardiac events include: normal P-waves, retrograde P-waves, R-waves, far-field QRS complexes, evoked potentials, T-waves, atrial fibrillation, atrial flutter, and exogenous noise (60 Hz).

Cardiac events are classified by determining the closest match between a set of measured feature values and the predetermined sets of reference values. The sets of feature values are compared to each of the sets of reference values at step 136 of FIG. 4. If a set of measured feature values for a cardiac event matches a certain reference value set, e.g., corresponding to a retrograde P-wave, then the cardiac event can be accurately classified as a retrograde P-wave.

Any suitable technique for comparing a set of feature values to the sets of reference values may be used. One measure of the degree of error in classifying events that may be used is given by Equation 1, which illustrates the calculation of classification error when there are three feature values and three reference values. If desired, any number of feature and reference values may be used.

$$\text{Classification\_Error} = |x - r_x| + |y - r_y| + |z - r_z| \qquad (1)$$

In Equation 1, x, y, and z make up a set of feature values and $r_x$, $r_y$, and $r_z$ make up a set of reference values. By minimizing the value of Classification_Error in Equation 1, the closest matching set of reference values can be identified for any given set of feature values.

If desired, statistically derived reference values may be provided as nominal reference values for the implantable cardiac device 10 (FIG. 1). The nominal reference values may be updated to reflect the signals that are actually measured for a particular patient. As shown in FIG. 4, the step 138 of updating the reference values may follow the successful classification of a cardiac event. For example, if a normal P-wave is detected, the values of the measured features can be averaged into the reference values, thereby updating the reference values to reflect the patient's present condition. Preferably, a physician can use an external programmer (not shown) to select whether or not the implantable cardiac device 10 (FIG. 1) should automatically update the reference values by incorporating recently measured feature values. Regardless of whether the reference values are automatically updated, the physician preferably has the option of manually updating the reference values at the step 138 (FIG. 4).

Figure 6:
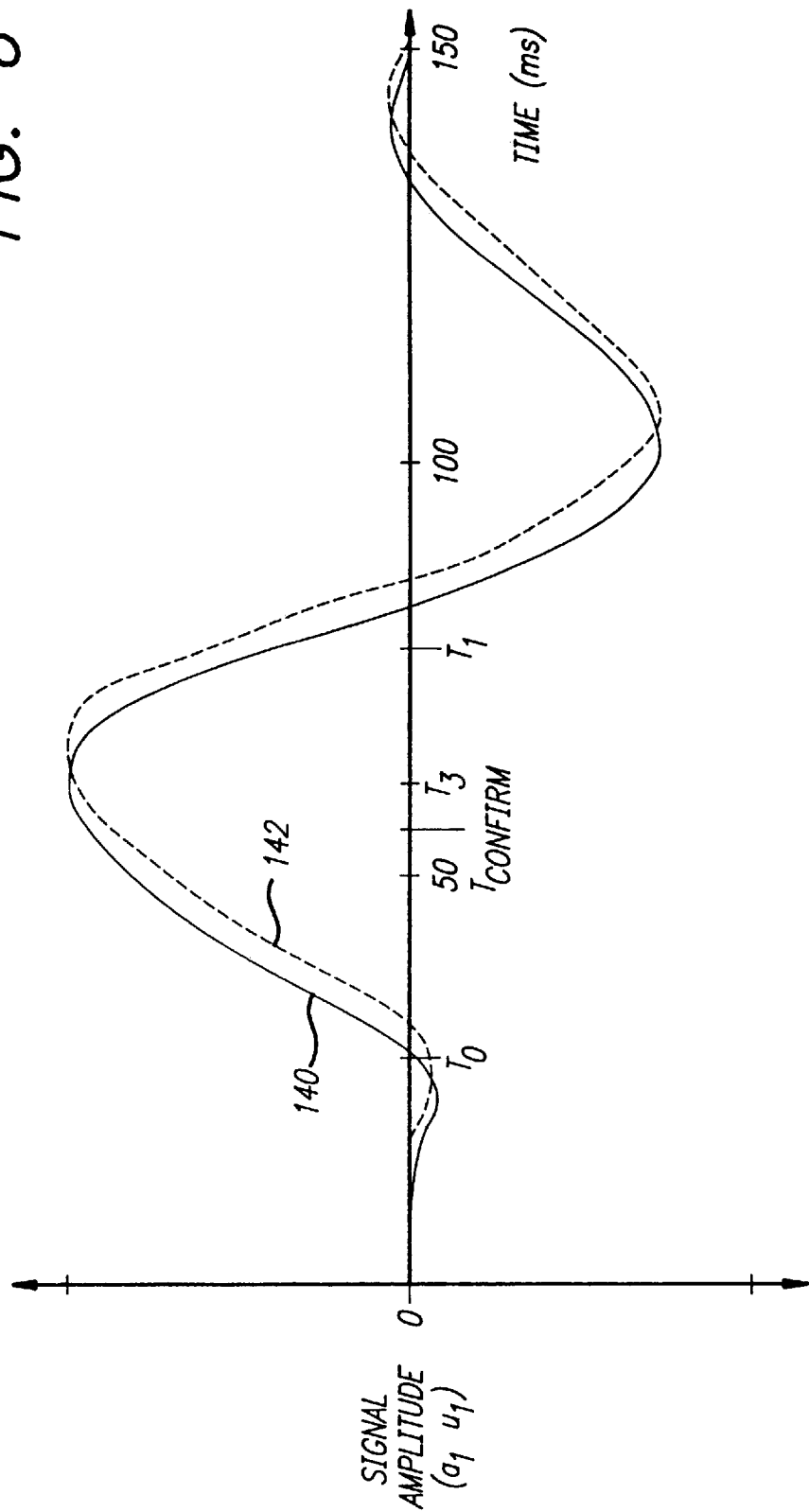
FIG. 6 is an idealized normal P-wave (the solid line represents the signal detected between the atrial ring electrode and the case electrode and the dashed line represents the signal detected between the ventricular ring electrode and the case electrode)
Figure 7:
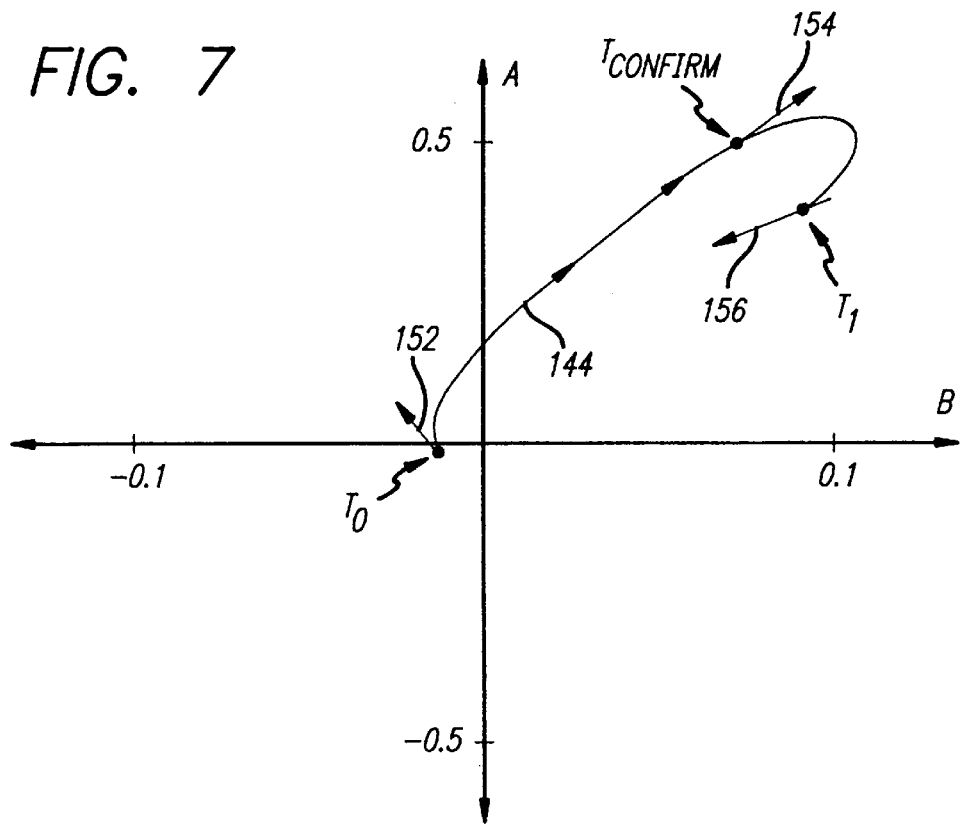
FIG. 7 is a graph in which the amplitude of the solid line of FIG. 6 is plotted along the A axis and the amplitude of the dashed line of FIG. 6 is plotted along the B axis.
Figure 9:
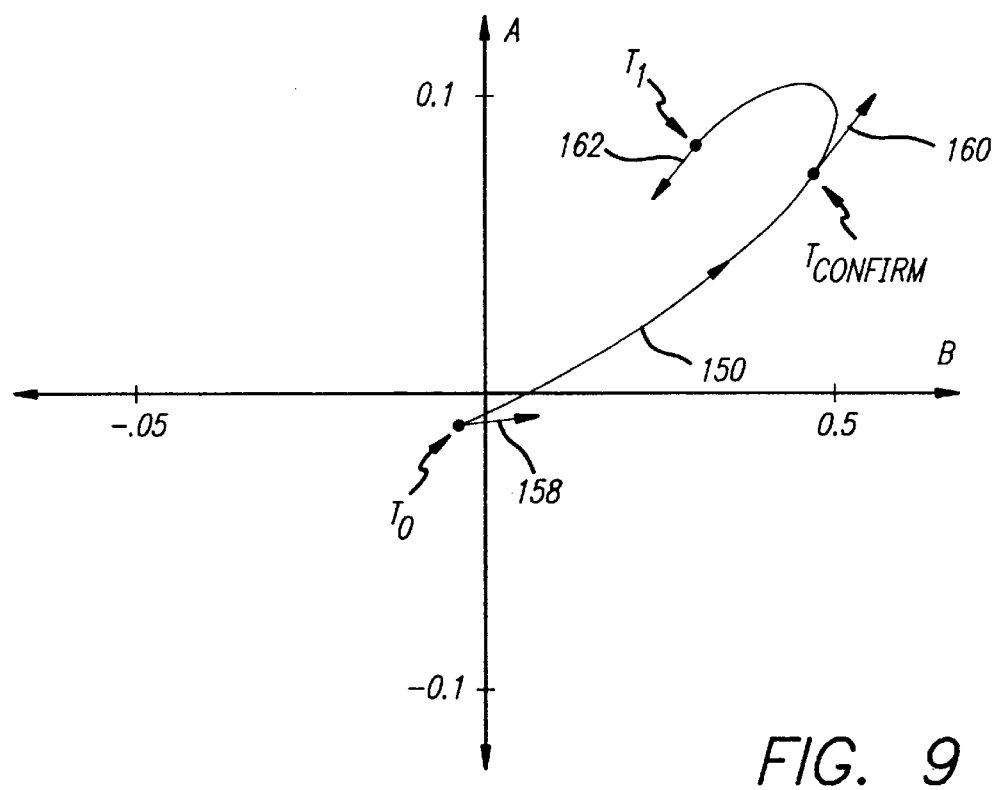
FIG. 9 is a graph in which the amplitude of the solid line of FIG. 8 is plotted along the A axis and the amplitude of the dashed line of FIG. 8 is plotted along the B axis.

Comparing cardiac data measured along one vector to that measured along another vector allows additional feature values to be generated for classifying the cardiac event. An illustrative example of the step 134 (FIG. 5) of calculating vector data to generate additional feature values is shown in FIGS. 6–9. An idealized normal P-wave measured along two different vectors is shown in FIG. 6. An idealized retrograde P-wave measured along the same two vectors is shown in FIG. 8. The relationship between the two vector signals of FIG. 6 is shown in FIG. 7, in which one of the signals is plotted along the vertical axis and the other along the horizontal axis. The relationship between the two vector signals of FIG. 8 is shown in FIG. 9, in which one of the signals is also plotted along the vertical axis and the other along the horizontal axis.

A cardiac signal 140 shown in FIG. 6 is measured between the atrial ring electrode 36 (FIG. 2) and the case electrode 44 (FIG. 2) along the vector 48. A cardiac signal 142 is measured between the ventricular ring electrode 40 (FIG. 2) and the case electrode 44 (FIG. 2) along the vector 50 (FIG. 2). The cardiac signal 140 across the atrial ring electrode 36 (FIG. 2) and the case electrode 44 (FIG. 2) is processed by the atrial sensing circuitry 54 (FIG. 3A) and the atrial intracardiac electrogram circuitry 58 (FIG. 3B). If desired, the atrial intracardiac electrogram circuitry 58 can be used to process a different cardiac signal than is being processed by the atrial sensing circuitry 54, which allows the arrangement of FIG. 3B to provide a greater number of cardiac signals to the control unit 24 (FIG. 1) for analysis than if the same cardiac signal is processed by both the atrial sensing circuitry 54 and the atrial intracardiac electrogram circuitry 58. The threshold detector 98 (FIG. 3B) generates an output pulse whenever a significant cardiac event is detected. The control unit 24 (FIG. 1) uses this output pulse to confirm the occurrence of a significant cardiac event at step 112 of FIG. 4. The time at which the significant cardiac event is confirmed is labelled $T_{CONFIRM}$ in FIG. 6.

The cardiac signal 140 of FIG. 6 is digitized by the atrial intracardiac electrogram circuitry 58 and stored in the buffer 28 (FIG. 1) by the control unit 24 (FIG. 1). When a significant cardiac event is confirmed at $T_{CONFIRM}$, the control unit 24 (FIG. 1) generates a set of feature values for the segment of the cardiac signal centered about this point. As shown in FIG. 6, the segment extends from a time $T_0$ to a time $T_1$. Preferably, the length of the segment $(T_1-T_0)$ and the position of the segment relative to $T_{CONFIRM}$ may be adjusted by the physician.

At the same time that the cardiac signal 140 is being measured, the cardiac signal 142 across the ventricular ring electrode 40 and the case electrode 44 (FIG. 2) is digitized by the ventricular intracardiac electrogram circuitry 60 and stored in the buffer 28 (FIG. 1) by the control unit 24 (FIG. 1). The ventricular sensing circuitry 56 (FIG. 3A) detects the occurrence of a significant cardiac event at $T_3$—shortly after the atrial sensing circuitry 54 (FIG. 3A) confirms the significant cardiac event at $T_{CONFIRM}$. The delay between $T_{CONFIRM}$ and $T_3$ is due the time required for an atrial cardiac signal to pass to the ventricles. Although the ventricular sensing circuitry 56 (FIG. 3A) passes a corresponding output pulse to the control unit 24 (FIG. 1), the control unit 24 (FIG. 1) preferably disregards this pulse, because the prior confirmation of the significant cardiac event by the atrial sensing circuitry 54 (FIG. 3A) at $T_{CONFIRM}$ is sufficient to indicate that the surrounding segment of cardiac data corresponds to a cardiac event that should be classified.

Following the confirmation of a significant cardiac event by the atrial sensing circuitry 54 (FIG. 3A) at $T_{CONFIRM}$, the control unit 24 (FIG. 1) preferably continues to store the digitized representation of the signals measured along vectors 48 and 50 (FIG. 2) in the buffer 28 (FIG. 1) until the time $T_1$. At $T_1$, the control unit 24 (FIG. 1) analyzes those portions of the cardiac signals 140 and 142 that fall within the segment extending from $T_0$ to $T_1$.

Any suitable technique for generating feature values by simultaneously processing and comparing the cardiac signals 140 and 142 may be used. A plot of the values of the cardiac signal 140 along the vertical axis A and the values of the cardiac signal 142 along the horizontal axis B is shown in FIG. 7. A curve 144 is formed by the plotting of the cardiac signals 140 and 142 (FIG. 6). The curve 144 exhibits a number of features that can be used to classify the type of cardiac event corresponding to the $T_0$ to $T_1$ segment of cardiac data. For example, the curve 144 originates in the third quadrant of the graph of FIG. 7 at time $T_0$, is in the first quadrant when the significant cardiac event is detected at $T_{CONFIRM}$, and terminates in the first quadrant at time $T_1$.

The quadrant of origination, the quadrant at $T_{CONFIRM}$, and the quadrant of termination are feature values obtained from the graph of FIG. 7 that can be used to characterize the $T_0$ to $T_1$ cardiac signal segment. Further, the curve 144 exhibits a clockwise rotation. Whether the curve 144 has a clockwise or a counterclockwise rotation is an additional feature that can be obtained from the $T_0$ to $T_1$ cardiac signal segment.

Retrograde P-waves, in contrast to normal P-waves, are ventricular rather than atrial in origin. This distinguishing aspect of retrograde P-wave signals can be detected by comparing the vector data measured for a retrograde P-wave to that of a normal P-wave. As shown in FIG. 8, the cardiac signal 146, which is measured between the ventricular ring electrode 40 (FIG. 2) and the case electrode 44 (FIG. 2) along the vector 50 (FIG. 2), leads the cardiac signal 148, which is measured between the atrial ring electrode 36 (FIG. 2) and the case electrode 44 (FIG. 2) along the vector 48 (FIG. 2).

A plot of the values of the cardiac signal 146 along the vertical axis A and the values of the cardiac signal 148 along the horizontal axis B is shown in FIG. 9 as curve 150. Feature values that may be calculated for the segment $T_0$ to $T_1$ of FIG. 8 based on the curve 150 of FIG. 9 include the initial quadrant (third), the quadrant at $T_{CONFIRM}$ (first), and the quadrant at termination (first). These features values are the same as those for the curve 144 in FIG. 7 for the normal P-wave. However, in contrast to the curve 144 of FIG. 7, the curve 150 of FIG. 9 advances in a counterclockwise rotation. The clockwise behavior of the curve 144 (FIG. 7) compared with the counterclockwise behavior of the curve 150 (FIG. 9) indicates that this feature value can be used to distinguish idealized normal P-waves from idealized retrograde P-waves.

In addition, feature values based on the trajectories of the curve 144 (FIG. 7) and the curve 150 (FIG. 9) can be calculated at various points. For example, the curve 144 of FIG. 7 has an initial trajectory 152 at $T_0$, a confirmation trajectory 154 at $T_{CONFIRM}$, and a final trajectory 156 at $T_1$. The curve 150 of FIG. 9 has an initial trajectory 158 at $T_0$, a confirmation trajectory 160 at $T_{CONFIRM}$, and a final trajectory 162 at $T_1$. Each of the trajectories for the curve 144 (FIG. 7) differs from the trajectories for curve 150 (FIG. 9), and is therefore a suitable feature value for distinguishing the normal P-wave of the curve 144 (FIG. 7) from the retrograde P-wave of the curve 150 (FIG. 9). Using conventional sensing circuitry it is not possible to distinguish these two types of P-waves, because both normal and retrograde P-waves have similar amplitudes and slew rates.

The step of calculating the vector data 134 (FIG. 5) using the vectors 48 and 50 (FIG. 2) thus generates a set of feature values that allows idealized normal P-waves to be distinguished from idealized retrograde P-waves. The vectors 48 and 50 may also be suitable for distinguishing normal and retrograde P-waves in practice. Preferably, the optimal vectors for distinguishing various cardiac events from one another are selected based on empirical studies.

Cardiac signals from the different vectors in a selected cardiac signal segment can be compared using any suitable technique. Cardiac signals can be compared by comparing the feature vectors described in connection with FIGS. 7 and 9 (quadrant, clockwise/counterclockwise rotation, and trajectory). If desired, cardiac signals measured along different vectors can also be compared by determining comparative maximum slew rates, maximum amplitudes, areas under the curve, etc. Regardless of the type of processing that is performed to generate the vector data at step 134 (FIG. 5), the resulting feature values may be used in conjunction with the feature values that are calculated in the steps 116–132 (FIG. 5) to generate a complete set of feature values in step 114 (FIG. 4).

If the implantable cardiac device 10 (FIG. 1) is a cardiac monitoring device, the additional information provided by the sets of feature values assists the physician in properly diagnosing the patient's condition. If the implantable cardiac device 10 (FIG. 1) is a pacemaker or cardioverter-defibrillator, the sets of feature values generated for each cardiac event allow more accurate classification of the nature of the cardiac events. Classifying cardiac events with greater precision ensures that the implantable cardiac device 10 (FIG. 1) can apply appropriate electrical stimulation to the patient's heart.

Thus, methods and apparatus are provided for classifying cardiac events with an implantable cardiac device. Cardiac signals are stored in a buffer. When a significant cardiac event is confirmed, a corresponding segment of the stored cardiac signals is processed to generate a set of feature values. The set of feature values is compared to various sets of reference values. Each set of reference values preferably corresponds to a separate type of cardiac event, so that the cardiac device may classify the significant cardiac event by matching its set of feature values to a set of reference values. Feature values include the maximum slew rate, the maximum signal amplitude, the time to reach the maximum positive and negative signal amplitudes, the area under the cardiac signal curve, the area under the cardiac signal curve above zero as compared to the area below zero, and the number of zero crossings made by the cardiac signal. Additional feature values are generated by simultaneously processing and comparing the cardiac signals measured along two different vector directions in the heart.

One skilled in the art will appreciate that the present invention can be practiced by other than the described embodiments, which are presented for the purposes of illustration and not of limitation, and the present invention is limited only by the claims that follow.

What is claimed is:

1. An implantable cardiac device for monitoring a cardiac signal from a patient's heart via leads connected to said heart, processing a segment of said cardiac signal that corresponds to a cardiac event, and classifying said cardiac event as being one of a plurality of possible types of cardiac events, each such possible type of cardiac event being characterized by a separate set of reference values, the implantable cardiac device comprising:

sensing circuitry connected to said leads for measuring said cardiac signals;

buffer means for storing said cardiac signals;

means for generating a set of feature values for said cardiac signal segment; and means for classifying said cardiac event by comparing said set of feature values to said sets of reference values to determine the closest match to said set of feature values from among said sets of reference values.

2. The implantable cardiac device of claim 1 further comprising means for confirming that said cardiac event has occurred.

3. The implantable cardiac device of claim 2 further comprising a threshold detector for detecting when said cardiac signals exceed a predetermined threshold.

4. The implantable cardiac device of claim 2 further comprising multiplexer means for selectively interconnecting said leads and said sensing circuitry.

5. The implantable cardiac device of claim 1 wherein said means for generating said set of feature values comprises means for generating a maximum positive amplitude feature value for said cardiac signal segment.

6. The implantable cardiac device of claim 5 wherein said means for generating said set of feature values further comprises means for generating a time to reach said maximum positive signal amplitude feature value for said cardiac signal segment.

7. The implantable cardiac device of claim 1 wherein said means for generating said set of feature values comprises means for generating a maximum negative amplitude feature value for said cardiac signal segment.

8. The implantable cardiac device of claim 7 wherein said means for generating said set of feature values further comprises means for generating a time to reach said maximum negative signal amplitude feature value for said cardiac signal segment.

9. The implantable cardiac device of claim 1 further comprising means for updating said reference values.

10. The implantable cardiac device of claim 1 wherein said buffer means comprises a circular buffer.

11. The implantable cardiac device of claim 1 wherein said means for generating said set of feature values comprises means for generating feature values selected from the group consisting of: maximum positive and negative slew rates exhibited by said cardiac signal segment, maximum positive and negative signal amplitudes exhibited by said cardiac signal segment, times to reach said maximum positive and negative signal amplitudes, area under said cardiac signal segment, area under said cardiac signal segment above zero as compared to area under said cardiac signal segment below zero, and number of zero crossings made by said cardiac signal segment.

12. The implantable cardiac device of claim 1 wherein said means for generating said set of feature values comprises means for generating a maximum positive slew rate feature value for said cardiac signal segment.

13. The implantable cardiac device of claim 1 wherein said means for generating said set of feature values comprises means for generating a maximum negative slew rate feature value for said cardiac signal segment.

14. The implantable cardiac device of claim 1 wherein said means for generating said set of feature values comprises means for generating an area under said cardiac signal segment feature value for said cardiac signal segment.

15. The implantable cardiac device of claim 1 wherein said means for generating said set of feature values comprises means for generating an area under said cardiac signal segment above zero as compared to area under said cardiac signal segment below zero feature value for said cardiac signal segment.

16. The implantable cardiac device of claim 1 wherein said means for generating said set of feature values comprises means for generating a number of zero crossings feature value for said cardiac signal segment.

17. The implantable cardiac device of claim 1 wherein:
said sensing circuitry comprises means for simultaneously measuring cardiac signals with a first pair of electrodes along a first vector in said heart and a second pair of electrodes along a second vector in said heart; and
said means for generating said set of feature values comprises means for comparing said cardiac signals measured along said first vector with said cardiac signals measured along said second vector.

18. The implantable cardiac device of claim 17 wherein said means for comparing comprises means for comparing said cardiac signals measured along said first and second vectors to generate feature values selected from the group consisting of: initial quadrant, confirmation quadrant, terminal quadrant, clockwise/counterclockwise rotation, initial trajectory, confirmation trajectory, terminal trajectory, comparative maximum slew rate, comparative maximum amplitude, comparative area under said cardiac signal segment, and comparative number of zero crossings.

19. The implantable cardiac device of claim 17 wherein said means for comparing comprises means for comparing said cardiac signals measured along said first and second vectors to generate an initial quadrant feature value for said cardiac signal segment.

20. The implantable cardiac device of claim 17 wherein said means for comparing comprises means for comparing said cardiac signals measured along said first and second vectors to generate a confirmation quadrant feature value for said cardiac signal segment.

21. The implantable cardiac device of claim 17 wherein said means for comparing comprises means for comparing said cardiac signals measured along said first and second vectors to generate a terminal quadrant feature value for said cardiac signal segment.

22. The implantable cardiac device of claim 17 wherein said means for comparing comprises means for comparing said cardiac signals measured along said first and second vectors to generate a clockwise/counterclockwise rotation feature value for said cardiac signal segment.

23. The implantable cardiac device of claim 17 wherein said means for comparing comprises means for comparing said cardiac signals measured along said first and second vectors to generate an initial trajectory feature value for said cardiac signal segment.

24. The implantable cardiac device of claim 17 wherein said means for comparing comprises means for comparing said cardiac signals measured along said first and second vectors to generate a confirmation trajectory feature value for said cardiac signal segment.

25. The implantable cardiac device of claim 17 wherein said means for comparing comprises means for comparing said cardiac signals measured along said first and second vectors to generate a terminal trajectory feature value for said cardiac signal segment.

26. The implantable cardiac device of claim 17 wherein said means for comparing comprises means for comparing said cardiac signals measured along said first and second vectors to generate a comparative maximum slew rate feature value for said cardiac signal segment.

27. The implantable cardiac device of claim 17 wherein said means for comparing comprises means for comparing said cardiac signals measured along said first and second vectors to generate a comparative maximum amplitude feature value for said cardiac signal segment.

28. The implantable cardiac device of claim 17 wherein said means for comparing comprises means for comparing said cardiac signals measured along said first and second vectors to generate a comparative area under said cardiac signal segment feature value for said cardiac signal segment.

29. The implantable cardiac device of claim 17 wherein said means for comparing comprises means for comparing said cardiac signals measured along said first and second vectors to generate a comparative number of zero crossings feature value for said cardiac signal segment.

30. A method for monitoring cardiac signals from a patient's heart with an implantable cardiac device having sensing circuitry connected to said heart via leads for receiving said cardiac signals and having a buffer in which a cardiac signal segment that corresponds to a cardiac event is stored, the method including the classification of said cardiac event as being one of a plurality of possible types of cardiac events, each such possible type of cardiac event being characterized by a separate set of reference values, the method comprising the steps of:
measuring said cardiac signals with said sensing circuitry;
storing said cardiac signals in said buffer;
generating a set of feature values for said cardiac signal segment; and
classifying said cardiac event by comparing said set of feature values to each of said sets of reference values to determine the closest match to said set of feature values from among said sets of reference values.

31. The method of claim 30 further comprising the step of confirming that said cardiac event has occurred.

32. The method of claim 30 wherein said step of generating said set of feature values comprises the step of generating feature values selected from the group consisting of: maximum positive and negative slew rates exhibited by said cardiac signal segment, maximum positive and negative signal amplitudes exhibited by said cardiac signal segment, times to reach said maximum positive and negative signal amplitudes, area under said cardiac signal segment, area under said cardiac signal segment above zero as compared to area under said cardiac signal segment below zero, and number of zero crossings made by said cardiac signal segment.

33. The method of claim 30 wherein said step of generating said set of feature values comprises the step of generating a maximum positive slew rate feature value for said cardiac signal segment.

34. The method of claim 30 wherein said step of generating said set of feature values comprises the step of generating a maximum negative slew rate feature value for said cardiac signal segment.

35. The method of claim 30 wherein said step of generating said set of feature values comprises the step of generating a maximum positive amplitude feature value for said cardiac signal segment.

36. The method of claim 30 wherein said step of generating said set of feature values comprises the step of generating a time to reach said maximum positive signal amplitude feature value for said cardiac signal segment.

37. The method of claim 30 wherein said step of generating said set of feature values comprises the step of generating a maximum negative amplitude feature value for said cardiac signal segment.

38. The method of claim 30 wherein said step of generating said set of feature values comprises the step of generating a time to reach said maximum negative signal amplitude feature value for said cardiac signal segment.

39. The method of claim 30 wherein said step of generating said set of feature values comprises the step of generating an area under said cardiac signal segment feature value for said cardiac signal segment.

40. The method of claim 30 wherein said step of generating said set of feature values comprises the step of generating an area under said cardiac signal segment above zero as compared to area under said cardiac signal segment below zero feature value for said cardiac signal segment.

41. The method of claim 30 wherein said step of generating said set of feature values comprises the step of generating a number of zero crossings feature value for said cardiac signal segment.

42. The method of claim 30 further comprising the step of updating said reference values.

43. The method of claim 30 wherein said step of storing said cardiac signals in said buffer comprises the step of storing said cardiac signals in a circular buffer.

44. The method of claim 30 further comprising the step of detecting when said cardiac signals exceed a predetermined threshold.

45. The method of claim 30 further comprising the step of selectively interconnecting said leads and said sensing circuitry with multiplexer circuitry.

46. The method of claim 30 further comprising the steps of:

using said sensing circuitry to simultaneously measure cardiac signals with a first pair of electrodes along a first vector in said heart and with a second pair of electrodes along a second vector in said heart; and comparing said cardiac signals measured along said first vector with said cardiac signals measured along said second vector to generate said set of feature values.

47. The method of claim 46 wherein said step of comparing comprises the step of comparing said cardiac signals measured along said first and second vectors to generate feature values selected from the group consisting of: initial quadrant, confirmation quadrant, terminal quadrant, clockwise/counterclockwise rotation, initial trajectory, confirmation trajectory, terminal trajectory, comparative maximum slew rate, comparative maximum amplitude, comparative area under said cardiac signal segment, and comparative number of zero crossings.

48. The method of claim 46 wherein said step of comparing comprises the step of comparing said cardiac signals measured along said first and second vectors to generate an initial quadrant feature value for said cardiac signal segment.

49. The method of claim 46 wherein said step of comparing comprises the step of comparing said cardiac signals measured along said first and second vectors to generate a confirmation quadrant feature value for said cardiac signal segment.

50. The method of claim 46 wherein said step of comparing comprises the step of comparing said cardiac signals measured along said first and second vectors to generate a terminal quadrant feature value for said cardiac signal segment.

51. The method of claim 46 wherein said step of comparing comprises the step of comparing said cardiac signals measured along said first and second vectors to generate a clockwise/counterclockwise rotation feature value for said cardiac signal segment.

52. The method of claim 46 wherein said step of comparing comprises the step of comparing said cardiac signals measured along said first and second vectors to generate an initial trajectory feature value for said cardiac signal segment.

53. The method of claim 46 wherein said step of comparing comprises the step of comparing said cardiac signals measured along said first and second vectors to generate a confirmation trajectory feature value for said cardiac signal segment.

54. The method of claim 46 wherein said step of comparing comprises the step of comparing said cardiac signals measured along said first and second vectors to generate a terminal trajectory feature value for said cardiac signal segment.

55. The method of claim 46 wherein said step of comparing comprises the step of comparing said cardiac signals measured along said first and second vectors to generate a comparative maximum slew rate feature value for said cardiac signal segment.

56. The method of claim 46 wherein said step of comparing comprises the step of comparing said cardiac signals measured along said first and second vectors to generate a comparative maximum amplitude feature value for said cardiac signal segment.

57. The method of claim 46 wherein said step of comparing comprises the step of comparing said cardiac signals measured along said first and second vectors to generate a comparative area under said cardiac signal segment feature value for said cardiac signal segment.

58. The method of claim 46 wherein said step of comparing comprises the step of comparing said cardiac signals measured along said first and second vectors to generate a comparative number of zero crossings feature value for said cardiac signal segment.

59. An implantable cardiac device for monitoring a cardiac signal from a patient's heart via leads connected to said heart, processing a segment of said cardiac signal that corresponds to a cardiac event, and classifying said cardiac event as being one of a plurality of possible types of cardiac events, each such possible type of cardiac event being characterized by a separate set of reference values, the implantable cardiac device comprising:

sensing circuitry, connected to said leads, for simultaneously measuring cardiac signals with a first pair of electrodes along a first vector in said heart and a second pair of electrodes along a second vector in said heart;

buffer means for storing said cardiac signals;

means for generating a set of feature values for said cardiac signal segment, said means for generating comprising means for comparing said cardiac signals measured along said first vector with said cardiac signals measured along said second vector; and means for classifying said cardiac event by comparing said set of feature values to said sets of reference values to determine the closest match to said set of feature values from among said sets of reference values.

60. A method for monitoring cardiac signals from a patient's heart with an implantable cardiac device having sensing circuitry connected to said heart via leads for receiving said cardiac signals and having a buffer in which a cardiac signal segment that corresponds to a cardiac event is stored, the method including the classification of said cardiac event as being one of a plurality of possible types of cardiac events, each such possible type of cardiac event being characterized by a separate set of reference values, the method comprising the steps of:

using said sensing circuitry to simultaneously measure cardiac signals with a first pair of electrodes along a first vector in said heart and with a second pair of electrodes along a second vector in said heart;

storing said cardiac signals in said buffer;

generating a set of feature values for said cardiac signal segment by comparing said cardiac signals measured along said first vector with said cardiac signals measured along said second vector; and classifying said cardiac event by comparing said set of feature values to each of said sets of reference values to determine the closest match to said set of feature values from among said sets of reference values.

61. An implantable cardiac device for monitoring a cardiac signal from a patient's heart via leads connected to said heart, processing a segment of said cardiac signal that corresponds to a cardiac event, and classifying said cardiac event as being one of a plurality of possible types of cardiac events, each such possible type of cardiac event being characterized by a separate set of reference values, the implantable cardiac device comprising:

sensing circuitry connected to said leads for measuring said cardiac signals;

buffer means for storing said cardiac signals;

means for generating a set of feature values for said cardiac signal segment, wherein the feature values are selected from the group consisting of:

a maximum positive slew rate, a maximum negative slew rate, a maximum positive signal amplitude, a maximum negative signal amplitude, a time to reach a maximum positive signal amplitude, a time to reach a maximum negative signal amplitude, an area under said cardiac signal segment, an area under said cardiac signal segment above zero as compared to an area under said cardiac signal segment below zero, and a number of zero crossings made by said cardiac signal segment; and means for classifying said cardiac event by comparing said set of feature values to said sets of reference values to determine the closest match to said set of feature values from among said sets of reference values.

62. The implantable cardiac device of claim 61, further comprising means for updating said reference values.

63. The implantable cardiac device of any of claims 61–62 wherein said buffer means comprises a circular buffer.

64. A method for monitoring cardiac signals from a patient's heart with an implantable cardiac device having sensing circuitry connected to said heart via leads for receiving said cardiac signals and having a buffer in which a cardiac signal segment that corresponds to a cardiac event is stored, the method including the classification of said cardiac event as being one of a plurality of possible types of cardiac events, each such possible type of cardiac event being characterized by a separate set of reference values, the method comprising the steps of:

measuring said cardiac signals with said sensing circuitry;

storing said cardiac signals in said buffer;

generating a set of feature values for said cardiac signal segment selected from the group of feature values consisting of:

a maximum positive slew rate, a maximum negative slew rate, a maximum positive signal amplitude, a maximum negative signal amplitude, a time to reach a maximum positive signal amplitude, a time to reach a maximum negative signal amplitude, an area under said cardiac signal segment, an area under said cardiac signal segment above zero as compared to an area under said cardiac signal segment below zero, and a number of zero crossings made by said cardiac signal segment; and classifying said cardiac event by comparing said set of feature values to each of said sets of reference values to determine the closest match to said set of feature values from among said sets of reference values.

* * * * *